United States Patent [19]

Burtner et al.

[11] Patent Number: 5,065,635

[45] Date of Patent: Nov. 19, 1991

[54] APPARATUS AND METHOD FOR INSPECTING AN ITEM HAVING GROOVES MACHINED THEREIN

[75] Inventors: Lee W. Burtner, Elizabeth Township, Allegheny County; David A. Chizmar, Washington Township, Westmoreland County, both of Pa.

[73] Assignee: Westinghouse Electric Corp., Pittsburgh, Pa.

[21] Appl. No.: 583,060

[22] Filed: Sep. 14, 1990

[51] Int. Cl.⁵ ............................................ G01R 33/00
[52] U.S. Cl. ................................................. 73/866.5
[58] Field of Search ........................... 73/12, 597–600, 73/649, 756, 621–625, 865.8, 866.5, 81–83, 865.5; 324/228, 234–238, 263

[56] References Cited

U.S. PATENT DOCUMENTS

| | | | |
|---|---|---|---|
| 4,368,642 | 1/1983 | Carodiskey | 73/623 |
| 4,375,165 | 3/1983 | de Sterke | 73/622 |
| 4,528,856 | 7/1985 | Junker et al. | 73/779 |
| 4,746,858 | 5/1988 | Metala et al. | 324/200 |
| 4,788,499 | 11/1989 | Meier et al. | 324/238 |
| 4,848,165 | 7/1989 | Bartilson et al. | 73/864.71 |
| 4,879,088 | 11/1989 | van Swam et al. | 73/622 |

FOREIGN PATENT DOCUMENTS 0126950 7/1984 Japan ................................. 73/598

Primary Examiner—Robert Raevis
Attorney, Agent, or Firm—K. Bach

[57] ABSTRACT

An apparatus for inspecting an item having grooves machined therein includes a main housing having longitudinal grooves formed in opposite sides thereof. The main housing defines an underside for contacting the item to be inspected. A carriage has opposite sides adapted for slidably engaging the longitudinal grooves in the main housing. A sensor is provided for inspecting the item. A mechanism is provided for connecting the sensor to the carriage such that the sensor extends beyond the underside of the main housing. The mechanism is adjustable so that the degree of extension of the sensor beyond the underside of the main housing may be controlled. A reference member is adjustably connected to, and extends from, the underside of the main housing for enabling the main housing to smoothly follow each groove.

9 Claims, 3 Drawing Sheets

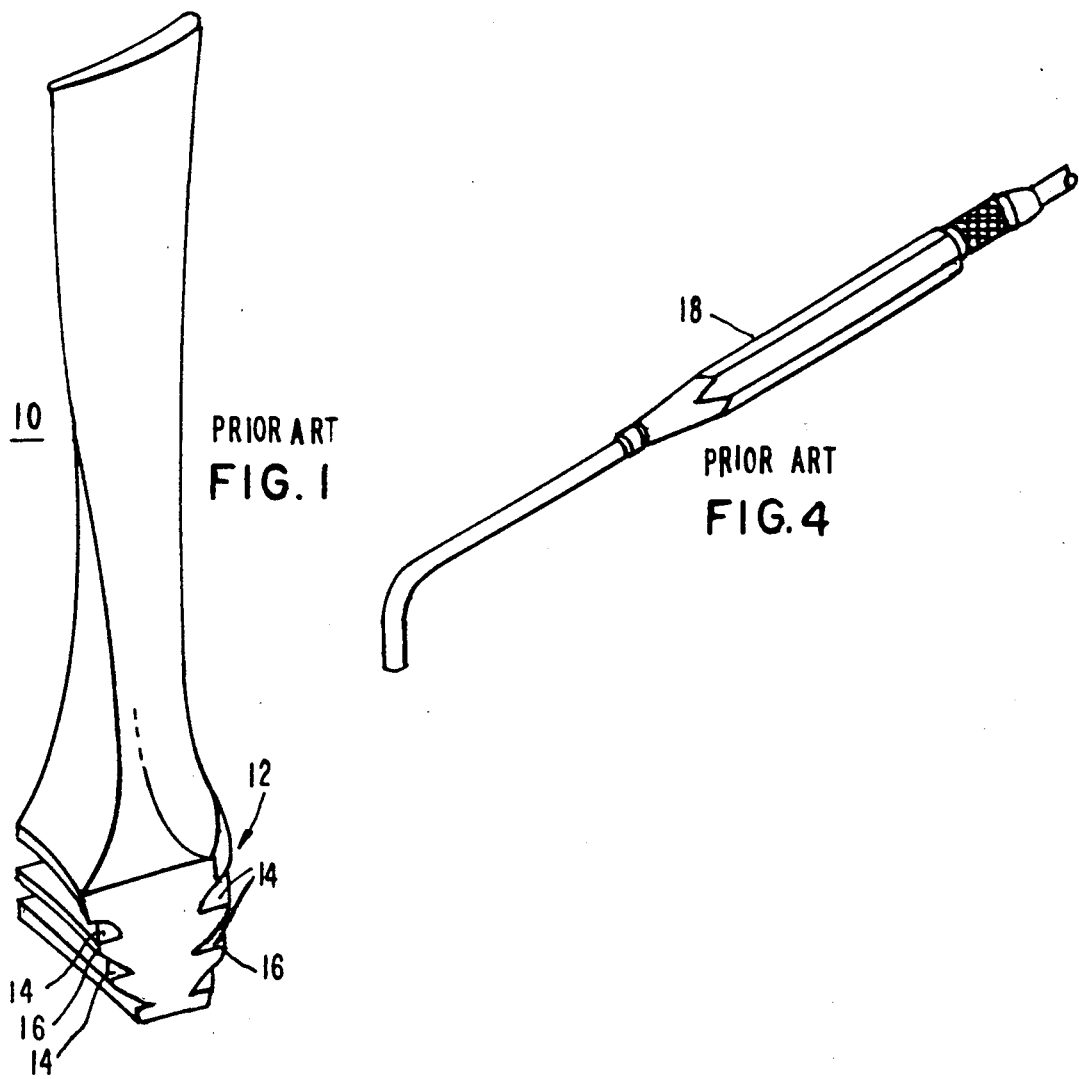
PRIOR ART
FIG. 1
PRIOR ART
FIG. 4
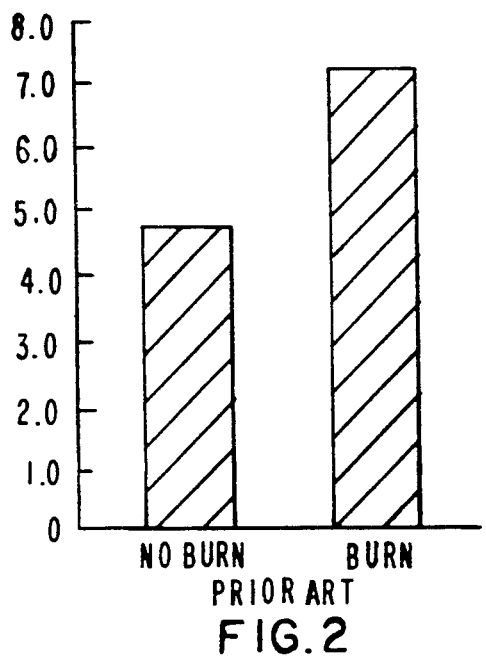
PRIOR ART
FIG. 2
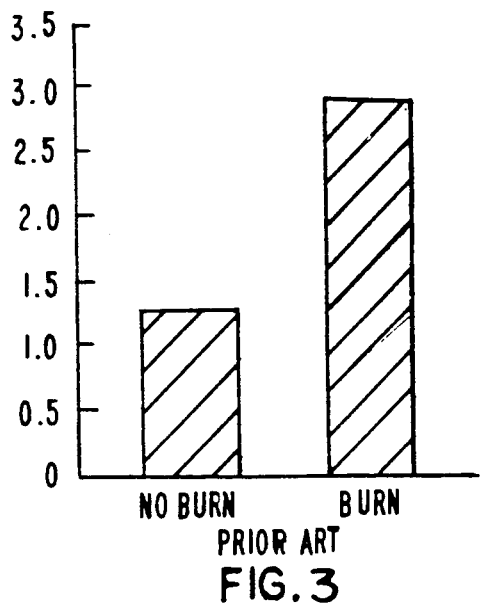
PRIOR ART
FIG. 3

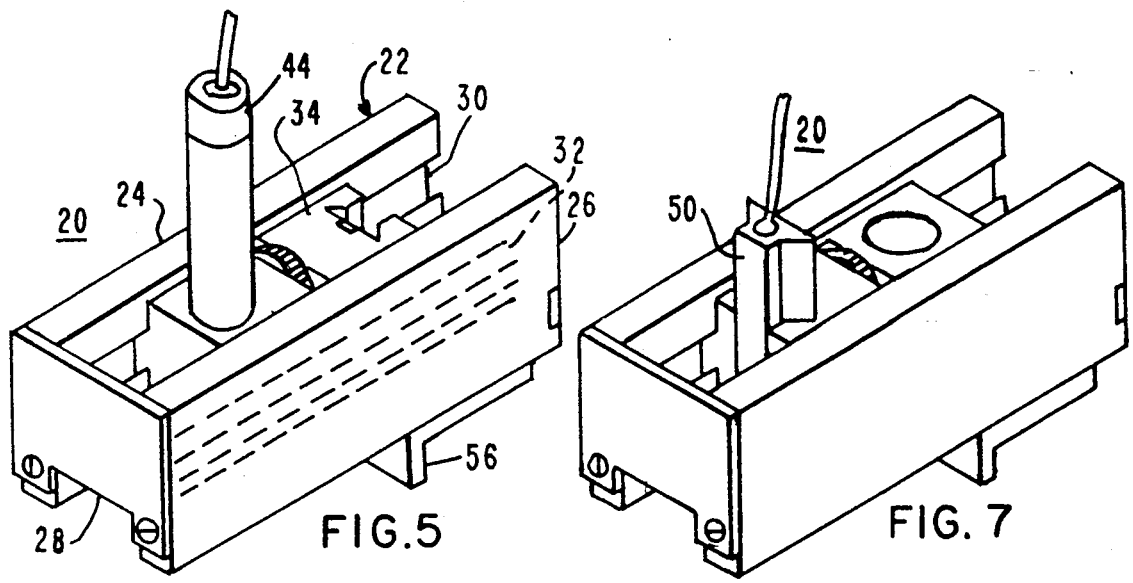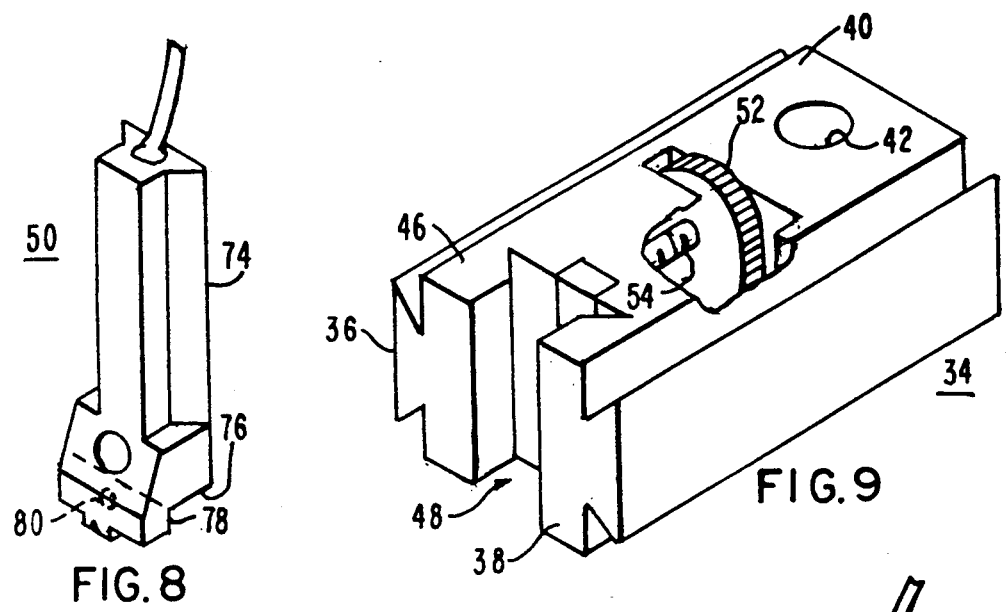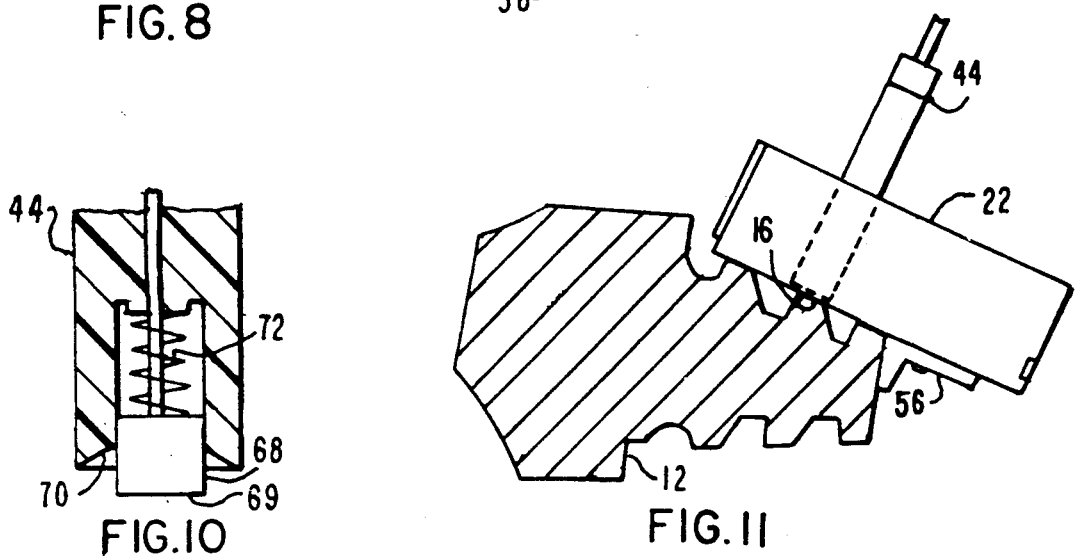

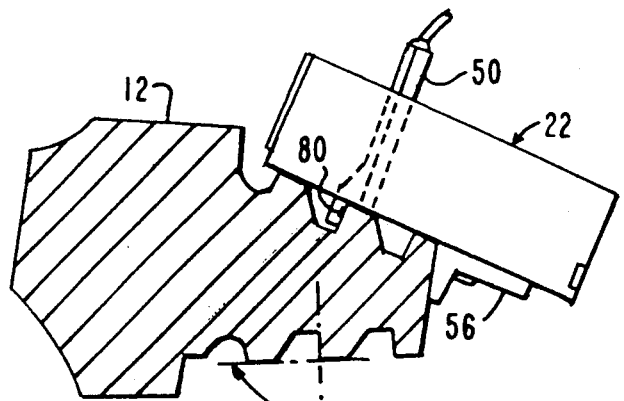
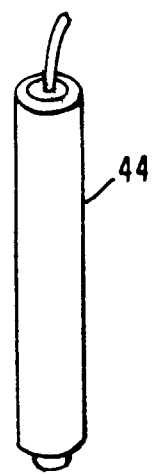
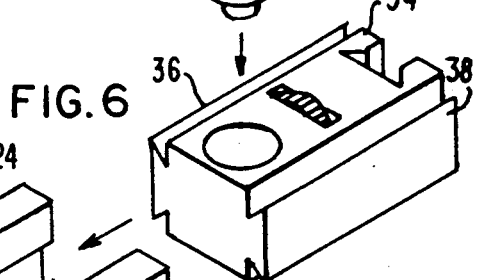
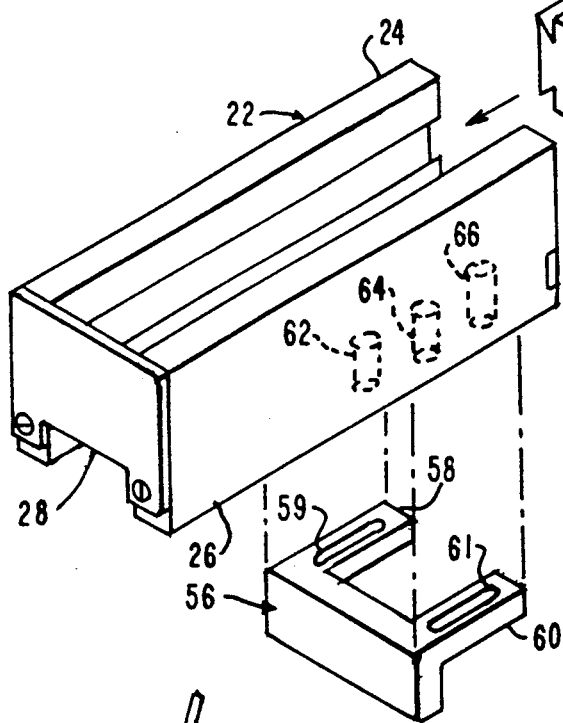
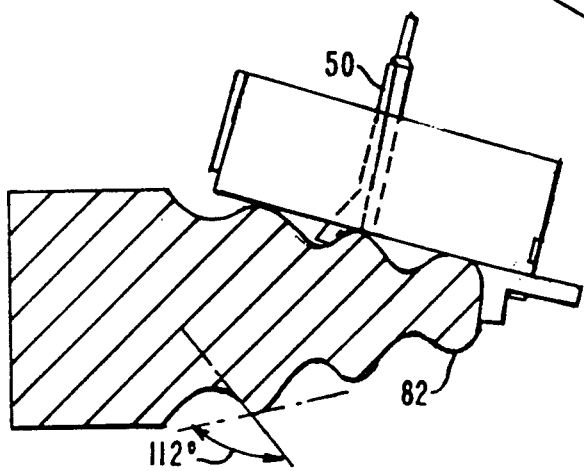

APPARATUS AND METHOD FOR INSPECTING AN ITEM HAVING GROOVES MACHINED THEREIN

BACKGROUND OF THE INVENTION

1. Field of the Invention

The present invention is directed generally to diagnostic equipment used to inspect manufactured goods and, more specifically, to diagnostic equipment used to 2. Description of the Prior Art FIG. 1 illustrates a steam turbine blade 10 of the type typically manufactured from near-net shape, high alloy, stainless steel forgings. Typically, the type of steel used may be ASTM Type 403, 17-4PH, or the like. Depending upon the specific application, the blades 10 may range in size from about four inches (10.16 cm) in length and a few pounds in weight to four feet in length (1.22 m) and one hundred lbs. in weight. The larger blades are often used in large industrial steam turbines. A critical step in the production of a blade 10 is the final machining of the blade attachment area or root 12. That final machining operation involves multiple pass grinding with shaped abrasive wheels.

During the grinding operation, a grinding burn may occur as a result of a lack of cooling of the blade root or a dull abrasive wheel. A grinding burn is an area of blade material which has been heated sufficiently to change or degrade the metallurgical properties of the steel, and, in turn, oxidize the surface of the metal. Because of the multiple passes of the grinding operation, a burn which could have been detected visually as a dark spot (oxidized material) on the root surface is removed by the subsequent grinding pass leaving damaged metal but no surface oxidation.

Following the multiple grinding operation, the root 12 is examined both visually and with dye penetrant or magnetic particle nondestructive inspection methods to insure that no surface discontinuities exist in the root 12 of the blade. Particular attention is focused on the load bearing surfaces 14 and the lands or flats 16 therebetween that will eventually be in direct contact with the turbine disk attachment area i.e. the fir tree or steeple region of the disk. However, because oxidation may have been removed by a subsequent grinding pass, a visual examination after machining will not reveal any degradation.

Recently, eddy current inspection procedures have been developed to supplement the optical examination and, in particular, to enhance the ability to detect grinding burns. As a result of a grinding burn, blade material is turned from ferrite to martensite. The eddy current procedures can detect residual damage because that change in microstructure produces a significant change in eddy current signature. FIG. 2 shows the difference in eddy current response for a burned and unburned 403 blade material with a yield strength of 136 ksi. FIG. 3 shows the difference in eddy current response for a burned and unburned type 403 blade material with a yield strength of 120 ksi. As can be seen, in both cases the burned material results in an output signal having a substantially greater magnitude than the output signal produced by the unburned material. Thus, eddy current sensors can be used to detect residual damage as a result of grinding burns.

An eddy current examination of the root 12 of the steam turbine blade 10 can be conducted manually by using a pencil probe 18 of the type illustrated in FIG. 4.

While pencil eddy current probes 18 of the type illustrated in FIG. 4 can detect and characterize grinding burn damage and other degradation in the root area of turbine blades, the procedures are slow and unreliable because the pencil probe 18 must be passed over all of the areas of interest thus making it likely that an area of interest will be skipped due to operator error. Thus, the need exists for an inspection device which is convenient, reliable, and can be used on a plurality of different blade roots and rotor steeples under production line conditions.

SUMMARY OF THE INVENTION

The present invention is directed to an apparatus and method for inspecting an item having grooves machined therein. The item may be, for example, the root of a turbine blade or the steeple carried by a rotor or a rotor disk. The apparatus is comprised of a main housing having longitudinal grooves formed in opposite interior sides thereof. The main housing defines an underside for contacting the item to be inspected. A carriage has opposite exterior sides adapted for slidably engaging the longitudinal grooves in the main housing. Sensors are provided for inspecting the item. The sensors are connected to the carriage in such a manner that the sensors extend beyond the underside of the main housing. A reference member is adjustably connected to, and extends from, the underside of the main housing to define where the sensor contacts the item to be inspected.

The present invention is also directed to a method of inspecting an item having grooves machined therein; the grooves define load bearing surfaces and flats therebetween. The method is comprised of the steps of positioning a first sensor within a carriage carried by a main housing so that the first sensor rides on a flat as the main housing is moved along a groove. The carriage is then repositioned so that another flat can be inspected as the main housing is moved along another groove. The carriage may be repositioned as many times as necessary until all of the flats have been inspected. A second sensor having a first surface for riding on a flat and a second inspecting surface for riding on a load bearing surface is then positioned so that the second inspecting surface rides on a load bearing surface as the main housing is moved along a groove. After inspection of that load bearing surface is completed, the carriage is repositioned so that another load bearing surface can be inspected. That process is repeated until all of the load bearing surfaces have been inspected.

The apparatus of the present invention provides several degrees of freedom in that the reference member can be adjusted, the position of the carriage can be adjusted, and the degree of extension of the sensors beyond the underside of the main housing can be adjusted. That provides the flexibility necessary to enable the present invention to be used with a plurality of different root and steeple configurations and sizes. The reference member also provides stability as the apparatus is moved along the grooves thereby ensuring that all of the surfaces of interest are inspected. Once the apparatus is adjusted for a particular root or steeple configuration, the testing of the surfaces of interest can be carried out quickly and efficiently. Those and other advantages and benefits of the present invention will become apparent from the Detailed Description of The Preferred Embodiment hereinbelow.

BRIEF DESCRIPTION OF THE DRAWINGS

For the present invention to be clearly understood and readily practiced, a preferred embodiment will now be described, by way of example only, with reference to the accompanying figures wherein:

FIG. 1 illustrates a steam turbine blade with which the inspection device of the present invention may be used;

FIG. 2 illustrates the signal produced by an eddy current sensor for a burned and unburned Type 403 blade material;

FIG. 3 is another example of the signal produced by an eddy current sensor for a burned and unburned Type 403 blade material;

FIG. 4 illustrates a prior art eddy current pencil probe;

FIG. 5 is a perspective view of an inspection device constructed according to the teachings of the present invention;

FIG. 6 is an exploded view of the inspection device illustrated in FIG. 5

FIG. 7 is a perspective view of the inspection device illustrated in FIG. 5 with the position of the carriage reversed and with a different eddy current sensor;

FIG. 8 is a perspective view of the eddy current sensor shown in FIG. 7;

FIG. 9 is a perspective view of the carriage;

FIG. 10 illustrates the tip of the eddy current sensor shown in FIG. 5;

FIGS. 11 and 12 illustrate how the inspection devices of FIGS. 5 and 7, respectively, may be used to inspect a particular blade root configuration; and FIG. 13 illustrates the inspection device of the present invention, carrying a different eddy current sensor, in conjunction with a different blade root configuration.

DETAILED DESCRIPTION OF THE PREFERRED EMBODIMENT

FIG. 5 is a perspective view of an inspection device 20 constructed according to the teachings of the present invention. FIG. 6 is an exploded view of the inspection device 20 illustrated in FIG. 5. The inspection device 20 is comprised of a main housing 22 which is generally rectangular in shape. The main housing 22 is constructed of opposing sides 24 and 26 connected by an end member 28. The side 24 has a dovetail-shaped groove 30 formed therein while the side 26 has a dovetail-shaped groove 32 formed therein.

The inspection device 20 is also comprised of a carriage 34 seen best in FIG. 9. The carriage 34 has a first wing-like member 36 extending from a side thereof which is configured to slidably engage groove 30 of the main housing 22 as seen in FIG. 6. The carriage 34 carries a second wing-like member 38 which extends oppositely from the first member 36. The second member 38 is configured to slidably engage the groove 32 of the main housing 24 as shown in FIG. 6. By virtue of the cooperation between the wing-like members 36 and 38 and the grooves 30 and 32, respectively, the carriage 34 can be positioned anywhere along the length of the main housing 22.

The carriage 34 has a first end 40 having an aperture 42 extending therethrough. The aperture 42 is adapted to receive a generally cylindrically shaped first sensor 44, which may be an eddy current type sensor. The first sensor 44 is seen best in FIGS. 5 and 6. The carriage 34 has a second end 46 having a slot 48 adapted to engage a second sensor 50, which may be an eddy current type sensor. The second sensor 50 is seen in FIGS. 7 and 8.

The carriage 34 also carries means for connecting the sensors 44 and 50 to the carriage 34 in such a manner that the sensors extend below the underside of the housing 22. The means for connecting may be comprised of a thumbwheel 52 carried on a threaded shaft 54. The thumbwheel 52 is positioned between aperture 42 and slot 48 and is held by the carriage 34 so that its position does not vary. Rotation of the thumbwheel 52 in one direction urges threaded shaft 54 toward the first probe 44 thereby locking the probe 44 in aperture 42. Rotation of thumbwheel 52 in the opposite direction urges threaded shaft 54 to engage the second sensor 50 thereby locking the second sensor 50 into slot 48. In that manner, the degree to which the sensors 44 and 50 extend beyond the underside of main housing 22 can be adjusted.

Completing the description of the apparatus 20 illustrated in FIGS. 5 and 6, a reference member 56 is connected to, and extends from, the underside of the main housing 22. The reference member 56 has a first leg 58 having a slot 59 therein which may be used to connect the reference member 56 to side 24 through the use of screws (not shown). The reference member 56 has a second leg 60 having a slot 61 therein which may be used to connect the second leg 60 to the side 26 of the main housing 22 through the use of screws (not shown). Each side 24, 26 of the main housing 22 may be provided with a plurality of tapped holes 62, 64, 66 for receiving screws for attaching reference member 56 to the main housing 22. Through the combination of tapped holes 62, 64, 66 and slots 59, 61 the reference member 56 may be positioned at any desirable location along the underside of main housing 22.

As is known, when grooves are machined, for example, in turbine blade root 10, load bearing surfaces 14 and flats or lands 16 therebetween are formed as shown in FIG. 1. The sensor 44, has a V-shaped tip 70, shown in FIG. 10, specifically designed for inspecting the flats 16. The sensor 44 carries a pancake type sensing coil (not shown) in a tip member 68. Tip member 68 is generally cylindrically shaped and has a flat surface 69 for riding on the flat 16 to be inspected. The generally V-shaped surface 70 has a diameter which is greater than the flat to be inspected thereby causing tip member 68 to be centered on such flats. Finally, a spring 72 may be provided to ensure that the tip member 68 is in constant contact with the flat being inspected.

The second sensor 50 is illustrated in FIG. 8. The second sensor 50 has a main body 74 shaped so as to be received in slot 48 of carriage 34. The second sensor 50 has a first surface 76 adapted for riding on flats 16. A second inspection surface 78 extends from the first surface at an angle which, for example, is 90°0 in FIG. 8. The second surface 78 is adapted for riding on load bearing surfaces 14. The second surface 78 carries a sensing coil 80 positioned to inspect the load bearing surface 14. The sensor 50 may have a single ferrite core (not shown) around which coil 80 is wrapped.

The first sensor 44 and second sensor 50 may be eddy current type sensors. The pancake coil (not shown) of sensor 44 and coil 80 of sensor 50 are provided with an excitation voltage from an external source thereby setting up a magnetic field. The magnetic field changes as the sensor is brought into contact with various materials, which in turn changes the characteristics of the coil. Those changes in characteristics result in a change in the output signal which is representative of the material with which the sensor is brought into contact. The electronics for driving such sensors and for analyzing the resulting output signals are well known. One example of such an eddy current instrument is made by Nortec, Model No. NDT-25L.

The operation of the present invention will now be described in conjunction with FIGS. 5 and 11 and 7 and 12. The sensor 44 is positioned in carriage 34 as shown in FIG. 5. Thereafter, the position of the carriage and/or reference member 56 is manipulated to enable the first sensor 44 to come into contact with one of the flats 16 as illustrated in FIG. 11. The housing 22 is then moved along the groove (i.e. in a direction perpendicular to the page as the root 12 is viewed in FIG. 11) thereby enabling sensor 44 to ride along flat 16 until the entire length of flat 16 is inspected. Reference member 56 prevents wobble of the main housing 22 and insures uniform and consistent results. After the flat 16 has been completely inspected, the carriage 34 and/or reference member 56 are manipulated so that the sensor 44 rests upon another flat 16. The main housing 22 is then moved along the groove so that that flat can be inspected by sensor 44. That process is repeated until all of the flats have been inspected.

After the flats have been inspected, first sensor 44 is removed and the position of the carriage 34 is reversed as shown in FIG. 7. With the carriage 34 oriented as shown in FIG. 7, the second sensor 50 is inserted into slot 48 and tightened therein by operation of thumbwheel 52. Referring to FIG. 12, the position of the carriage 34 and/or reference member 56 is adjusted to enable the first surface 76 of the second sensor 50 to ride on a flat 16 while the inspection surface 78 of the sensor 50 rides along load bearing surface 14. Thereafter, movement of the inspection device 20 along the groove enables the load bearing surface 14 to be inspected. Each load bearing surface is inspected in a similar manner until all surfaces have been inspected.

FIG. 13 illustrates an alternative embodiment of the present invention. In FIG. 13, the sensor 50 is provided with a first surface 76 and a second inspection surface 78 which are at an angle of 112° with respect to one another. That difference in sensor 50 allows the inspection device 20 of the present invention to be used in conjunction with a root 82 configurated as illustrated in FIG. 13.

Because of the multiple degrees of freedom offered by the present invention, i.e. movement of the carriage 34, adjustability of reference member 56, and adjustability of the degree to which sensors 44 and 50 extend beyond the underside of the main housing 22, the apparatus 20 of the present invention provides sufficient elevational and lateral adjustment to enable it to be used with a variety of root configurations and sizes. The present invention may be used equally well on both the concave and convex sides of a root. Additionally, depending upon the size of the present invention, it may also be used to inspect steeples of rotor disks or rotors. The present invention thus provides a quick and easy apparatus and method for inspecting for disk continuities such as grinding burns in the machined parts.

While the present invention has been described in connection with exemplary embodiments thereof, it will be understood that many modifications and variations will be readily apparent to those of ordinary skill in the art. This disclosure and the following claims are intended to cover all such modifications and variations.

What is claimed is:

1. An apparatus for inspecting an item having grooves machined therein, said apparatus comprising:
   a main housing having longitudinal grooves formed in opposite sides thereof, said main housing defining an underside for contacting the item to be inspected;
   a carriage having opposite sides adapted for slidably engaging said longitudinal grooves in said main housing;
   sensor means for inspecting the item;
   means for connecting said sensor means to said carriage such that said sensor means extends beyond said underside of said main housing, said means for connecting being adjustable for controlling the degree of extension; and
   reference member means adjustably connected to and extending from said underside of said main housing for enabling uniform and consistent contact of said sensor means with the item to be inspected.

2. An apparatus as claimed in claim 1 wherein the item to be inspected includes load bearing surfaces and flats therebetween, and wherein said sensor means alternately includes a first sensor for inspecting the flats and a second sensor for inspecting the load bearing surfaces.

3. An apparatus as claimed in claim 2 wherein said carriage includes an aperture in a first end thereof for receiving said first sensor and a slot at a second end thereof for engaging said second sensor.

4. An apparatus as claimed in claim 3 wherein said means for connecting includes a thumbwheel carried on a threaded shaft, said thumbwheel and said threaded shaft being carried by said carriage and positioned between said aperture and said slot such that rotation of said thumbwheel in one direction urges said shaft into engagement with said first sensor and rotation of said thumbwheel in an opposite direction urges said shaft into engagement with said second sensor.

5. An apparatus as claimed in claim 2 wherein said first sensor includes a tip member and a spring for urging said tip member into engagement with the flats.

6. An apparatus as claimed in claim 5 wherein said first sensor has a V-shaped surface for centering said first sensor on the flats.

7. An apparatus as claimed in claim 2 wherein said second sensor includes a first surface adapted to engage the flats and a second inspection surface, extending at an angle from said first surface, adapted to engage the load bearing surfaces.

8. An apparatus as claimed in claim 7 wherein said angle between said first surface and said second surface is ninety degrees.

9. An apparatus as claimed in claim 7 wherein said angle between said first surface and said second surface is one hundred twelve degrees.

* * * * *